US009661989B2

(12) United States Patent
Secrest et al.

(10) Patent No.: US 9,661,989 B2
(45) Date of Patent: May 30, 2017

(54) OVERTUBE ASSEMBLY (75) Inventors: Dean J. Secrest, Concord, OH (US); K. Randall John, Chardon, OH (US); Christopher J. Kaye, Concord, OH (US)

(73) Assignee: U.S. ENDOSCOPY GROUP, INC., Mentor, OH (US)

( * ) Notice: Subject to any disclaimer, the term of this patent is extended or adjusted under 35 U.S.C. 154(b) by 1286 days.

(21) Appl. No.: 11/141,450

(22) Filed: May 31, 2005

(65) Prior Publication Data

US 2005/0267331 A1 Dec. 1, 2005

Related U.S. Application Data (60) Provisional application No. 60/575,260, filed on May 28, 2004.

(51) Int. Cl.
*A61B 1/04* (2006.01)
*A61B 1/00* (2006.01)
(Continued)

(52) U.S. Cl.
CPC .......... *A61B 1/00154* (2013.01); *A61B 1/273* (2013.01); *A61B 17/3421* (2013.01);
(Continued)

(58) Field of Classification Search
CPC ..... A61B 1/267; A61B 1/2673; A61B 1/2676; A61B 1/00154; A61B 1/273; A61B 17/3468; A61B 17/3431
(Continued)

(56) References Cited

U.S. PATENT DOCUMENTS 4,580,556 A * 4/1986 Kondur .................... 128/206.28
4,657,020 A * 4/1987 Lifton ........................... 606/106
(Continued)

FOREIGN PATENT DOCUMENTS

JP 4263870 9/1992
JP 07051221 2/1995

OTHER PUBLICATIONS

Giorgio Bertoni et al., Endoscopic protector hood for safe removal of sharp-pointed gastroesophageall foreign bodies; Surgical Endoscopy (1992) 6: pp. 255-258.
(Continued)

*Primary Examiner* — Timothy J Neal
(74) *Attorney, Agent, or Firm* — Calfee Halter & Griswold LLP (57) ABSTRACT An overtube device for use in intubation during an endoscopic procedure is disclosed. The device includes an outer tube and an inner tube. The outer tube includes a distal end, a proximal end, and a first handle disposed on the proximal end. The inner tube includes a distal end, a proximal end, and a second handle disposed on the proximal end. The inner tube is inserted through an entire length of the outer tube such that the inner tube extends beyond the outer tube. At the proximal end of the device, a proximal end of the first handle is connected to a distal end of the second handle. When the inner tube is co-axially inserted within the outer tube, a clearance exists between a length of the inner and outer tubes, and between a length of the inner tube and the endoscope. Methods of use are disclosed.

10 Claims, 11 Drawing Sheets (51) Int. Cl.
  *A61B 1/273* (2006.01)
  *A61B 17/34* (2006.01)
  *A61B 90/00* (2016.01)

(52) U.S. Cl.
  CPC ...... *A61B 17/3431* (2013.01); *A61B 17/3468* (2013.01); *A61B 17/3496* (2013.01); *A61B 17/3498* (2013.01); *A61B 2090/062* (2016.02)

(58) Field of Classification Search
  USPC ....... 600/120, 104, 114, 121, 186, 194, 127, 600/129, 154, 117, 123–125, 185, 150, 600/156, 115–116; 128/898; 604/272, 604/264
  See application file for complete search history.

(56) References Cited

U.S. PATENT DOCUMENTS

| | | | |
|---|---|---|---|
| 4,815,450 A * | 3/1989 | Patel | 600/115 |
| 4,846,153 A * | 7/1989 | Berci | 600/109 |
| 4,913,139 A * | 4/1990 | Ballew | 128/200.11 |
| 5,037,386 A | 8/1991 | Marcus et al. | |
| 5,112,308 A | 5/1992 | Olsen et al. | |
| 5,203,320 A * | 4/1993 | Augustine | 600/187 |
| 5,279,610 A * | 1/1994 | Park et al. | 606/108 |
| 5,287,845 A * | 2/1994 | Faul et al. | 600/135 |
| 5,337,733 A | 8/1994 | Bauerfeind et al. | |
| 5,342,315 A | 8/1994 | Rowe et al. | |
| 5,392,766 A * | 2/1995 | Masterson et al. | 600/157 |
| 5,397,335 A | 3/1995 | Gresl et al. | |
| 5,628,732 A | 5/1997 | Antoon, Jr. et al. | |
| 5,632,761 A * | 5/1997 | Smith et al. | 606/192 |
| 5,643,174 A * | 7/1997 | Yamamoto et al. | 600/114 |
| 5,657,963 A | 8/1997 | Hinchliffe et al. | |
| 5,759,185 A | 6/1998 | Grinberg | |
| 5,779,624 A | 7/1998 | Chang | |
| 5,846,182 A * | 12/1998 | Wolcott | 600/114 |
| 5,855,569 A * | 1/1999 | Komi | 604/526 |
| 5,941,815 A * | 8/1999 | Chang | 600/114 |
| 5,954,636 A * | 9/1999 | Schwartz et al. | 600/120 |
| 6,079,409 A * | 6/2000 | Brain | 128/200.26 |
| 6,197,002 B1 | 3/2001 | Peterson | |
| 6,200,262 B1 | 3/2001 | Ouchi | |
| 6,210,378 B1 * | 4/2001 | Ouchi | 604/264 |
| 6,217,557 B1 * | 4/2001 | Håkansson et al. | 604/167.06 |
| 6,322,538 B1 | 11/2001 | Elbert et al. | |
| 6,361,540 B1 | 3/2002 | Gauderer et al. | |
| RE37,772 E * | 6/2002 | Kelleher | 600/104 |
| 6,419,628 B1 | 7/2002 | Rudischhauser et al. | |
| 6,470,888 B1 * | 10/2002 | Matter | 128/207.14 |
| 6,482,181 B1 | 11/2002 | Racenet et al. | |
| 6,503,196 B1 | 1/2003 | Kehr et al. | |
| 6,508,757 B1 * | 1/2003 | Song et al. | 600/120 |
| 6,543,446 B1 * | 4/2003 | Christopher | 128/200.26 |
| 6,551,282 B1 * | 4/2003 | Exline et al. | 604/167.01 |
| 6,585,639 B1 * | 7/2003 | Kotmel et al. | 600/116 |
| 6,615,835 B1 * | 9/2003 | Cise et al. | 128/207.14 |
| 6,638,289 B1 | 10/2003 | Johnson et al. | |
| 6,656,153 B1 | 12/2003 | Sakai et al. | |
| 6,663,646 B1 * | 12/2003 | Shah | 606/192 |
| 6,689,086 B1 | 2/2004 | Nita et al. | |
| 6,827,710 B1 | 12/2004 | Mooney et al. | |
| 6,978,784 B2 * | 12/2005 | Pekar | 128/207.14 |
| 7,708,713 B2 * | 5/2010 | Albrecht et al. | 604/23 |
| 2001/0023333 A1 * | 9/2001 | Wise et al. | 604/101.01 |
| 2002/0096177 A1 * | 7/2002 | Toti et al. | 128/207.15 |
| 2003/0083546 A1 * | 5/2003 | Butler et al. | 600/114 |
| 2003/0144577 A1 | 7/2003 | Bacher et al. | |
| 2003/0216615 A1 | 11/2003 | Ouchi | |
| 2004/0064130 A1 | 4/2004 | Carter | |
| 2004/0082905 A1 | 4/2004 | Solar et al. | |
| 2004/0147866 A1 * | 7/2004 | Blatter et al. | 604/6.16 |
| 2004/0158136 A1 * | 8/2004 | Gough et al. | 600/328 |
| 2004/0199047 A1 | 10/2004 | Taimisto et al. | |
| 2005/0175067 A1 * | 8/2005 | Chu | 374/208 |

OTHER PUBLICATIONS

A device to improve the feed of a flexible endoscipe; http://www.amichael.de/Endoskoptextengl.htm; Feb. 20, 2003, pp. 1-10.
International Search Report and Written Opinion of the International Searching Authority from International Application No. PCT/US05/18818, mailed Jun. 23, 2008.
English translation of Office Action from Japanese Application No. 2007-515410, dated Nov. 26, 2010, 8 pages.

* cited by examiner

OVERTUBE ASSEMBLY

CROSS-REFERENCE TO RELATED APPLICATIONS

This non-provisional application claims the benefit of U.S. Provisional Patent Application No. 60/575,260, entitled "Overtube Assembly," filed May 28, 2004, which is hereby incorporated in its entirety.

FIELD OF THE INVENTION

The present invention relates to an overtube assembly and more particularly to an overtube assembly for use in intubating a human subject as part of an endoscopic procedure.

BACKGROUND OF THE INVENTION

Endoscopes are well-known in the art and are commonly used for numerous medical procedures that involve intubation of the esophagus and gastro-intestinal tract. As such, many devices and accessory instruments have been developed that relate to the operation of an endoscope. Devices that aid a physician in intubation, such as an overtube, are one such type of device in the endoscopic art field.

In general, an overtube may be used by a physician during an endoscopic procedure. An endoscope is inserted within an overtube, and then the assembly is inserted into a patient's esophagus. The overtube remains in place within a patient's esophagus, while the endoscope may be inserted and removed many times, during a so-called multiple intubation procedure. This technique is designed to reduce damage to the esophagus otherwise caused by repeated insertions. However, physicians have expressed their concerns regarding the design of conventional overtubes. Specifically, the complaints center on a small annular gap existing between the distal end of the overtube and the endoscope. Mucosal tissue may become pinched or trapped in this gap during initial insertion, causing severe damage to the esophagus. Tearing of the submucosal and/or muscularis layer is also possible. As such, clinical use of overtubes in general has reduced significantly. Therefore, a need exists in the art for an overtube assembly design that does not cause mucosal tissue damage.

The present invention is an improved intubation assembly that includes an inner tube and an outer tube. The overtube assembly provides a device for aiding intubation that reduces damage to the mucosal tissue, maintains a proximal end seal to maintain consistent insufflation and minimize leakage of bodily fluids during procedure, offers a convenient intubation method, and reduces the overall time of the endoscopic procedure. Other benefits of the present invention include an expandable distal end of the outer tube to accommodate oversized foreign objects and distance markings on the outer tube.

SUMMARY OF THE INVENTION

In an embodiment of the present invention, an overtube assembly for use in intubating a human subject as part of an endoscopic procedure is disclosed. Use of the device avoids pinching of the esophagus mucosa layer during intubation. Method of use are also disclosed. It should be apparent to others with ordinary skill in the art that use of this assembly is not limited to the esophagus intubations, but may also include gastric, small bowel, and colonic intubations and trans-oral, trans-gastric surgeries.

The overtube includes a outer tube, an inner tube, and a seal cap. The outer tube includes an elongated tube having a distal end, a proximal end, and a first handle disposed on the proximal end. The inner tube includes an elongated tube having a distal end, a proximal end, and a second handle disposed on the proximal end. The inner tube is inserted through an entire length of the outer tube such that inner tube distal end extends beyond the outer tube distal end. A proximal end of the first handle is connected to a distal end of the second handle. With the second handle removed, the seal cap is adapted to form a seal with the proximal end of the first handle.

Further features and advantages of the invention will become apparent from the following detailed description made with reference to the accompanying drawings.

The Detailed Description of the Invention merely describes preferred embodiments of the invention and is not intended to limit the scope of the claims in any way. Indeed, the invention as described by the claims is broader than and unlimited by the preferred embodiments, and the terms in the claims have their full ordinary meaning.

BRIEF DESCRIPTION OF THE DRAWINGS

FIG. 4b is a schematic view of the device of FIG. 1, showing a human patient intubated with the assembly shown in FIG. 4a;

FIG. 5a is an enlarged cross-sectional view of the assembly of FIG. 4a, showing an endoscope inserted therethrough;

FIG. 5b is a schematic view of the device of FIG. 1, showing a human patient intubated with the assembly shown in FIG. 5a;

DESCRIPTION OF THE INVENTION

An overtube device for use in intubating a human subject as part of an endoscopic procedure is disclosed. Hereinafter, the terms "inner tube" and "outer tube" are used to describe two separate items, and the term "overtube device" is used to describe an assembly unless otherwise noted. Further, it should be understood by one with ordinary skill in the art that the relative size of the assembly shown is for exemplary purposes only, and the present invention is applicable with a wide range of endoscope sizes.

In discussing the assembly, the terms distal and proximal are used with respect to the perspective of the operator. In other words, when the device is used in connection with an endoscope or other medical device, the proximal and distal orientation are relative to the surgeon or operator of the device.

Figure 1:
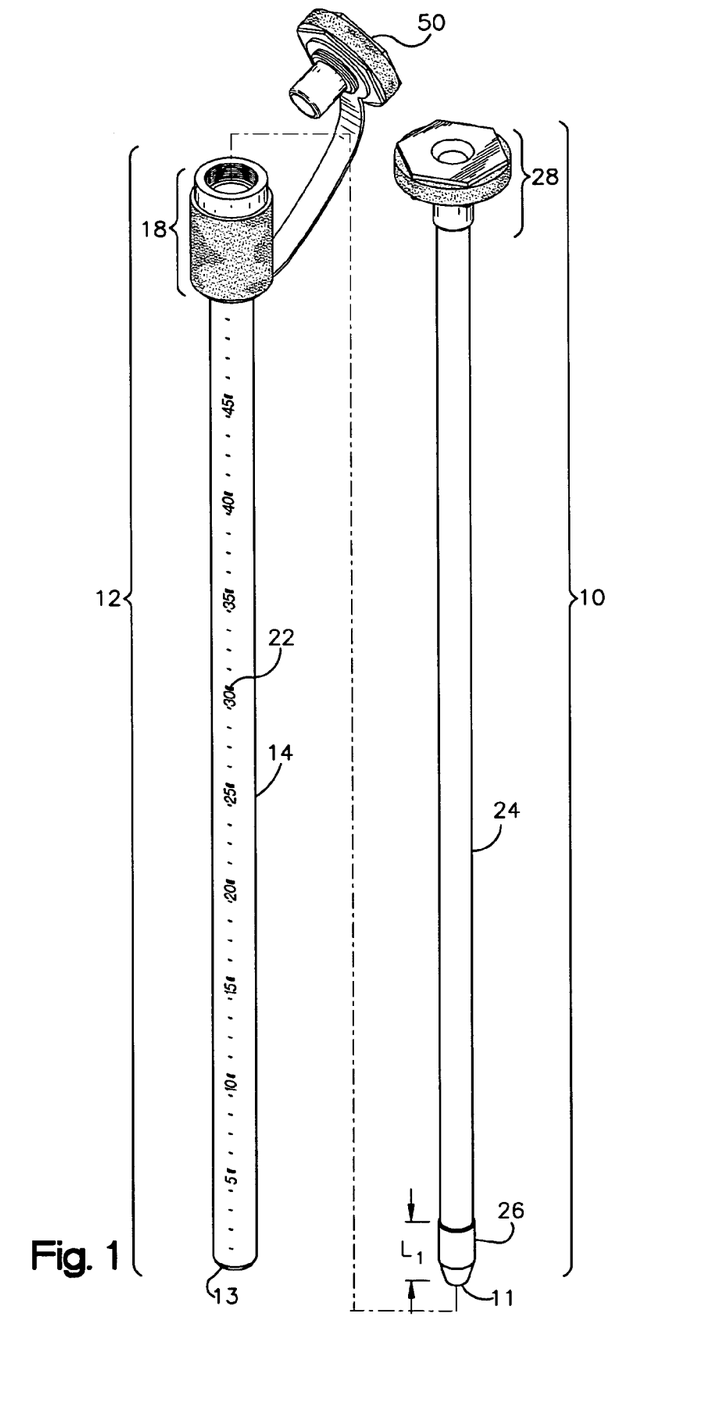
FIG. 1 is a perspective assembly view of an overtube device constructed in accordance with an embodiment of the present invention, showing an inner tube and an outer tube in a separated position.
Figures 2A, 2B:
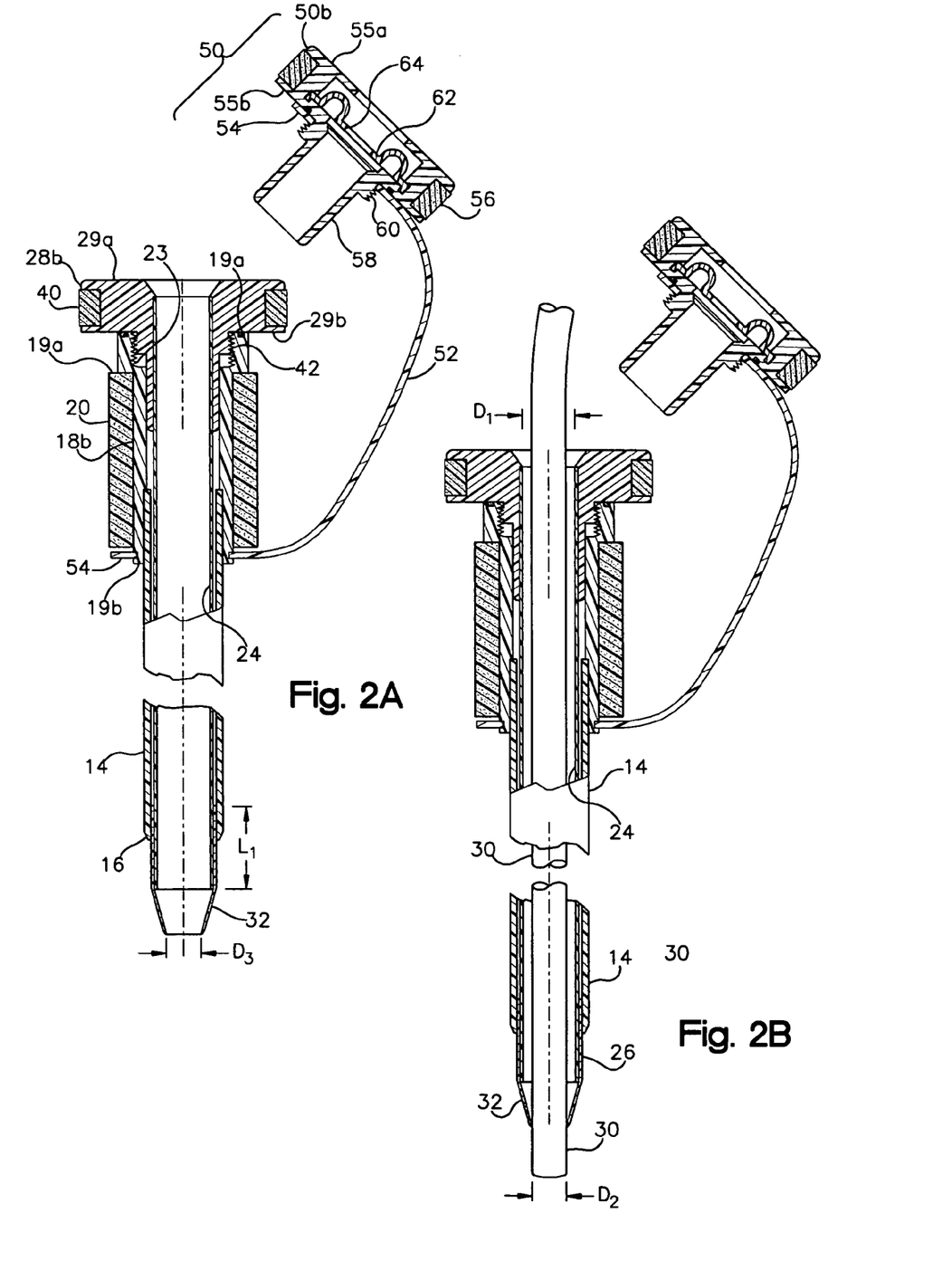
FIG. 2a is an enlarged cross-sectional view of the device of FIG. 1, showing the inner tube and outer tube in an assembled position.
FIG. 2b is an enlarged cross-sectional view of the device of FIG. 1, showing the inner tube and outer tube in an assembled position with an endoscope inserted through the inner tube.

Referring now to the Figures, a perspective assembly view of an overtube device constructed in accordance with an embodiment of the present invention is shown in FIG. 1. Specifically, an inner tube 10, an outer tube 12 and a tethered cap 50 are illustrated in a separated position. The tubes form an overtube device for use in intubating a human subject as part of a procedure using an endoscope. FIG. 2a is an enlarged cross-sectional view of the device of FIG. 1, showing the inner tube 10 and outer tube 12 in an assembled position.

The outer tube 12 includes an elongated tube 14, a tapered portion 16 disposed on the tube 14 distal end, and a first handle 18 disposed on the tube 14 proximal end. The elongated tube 14 may include length identifying indicia 22. As shown, the indicia 22 are a series of equally spaced length markings on the outer tube. These markings allow a physician to monitor depth during initial insertion of the elongated tube 14, as well as to monitor any migration of the assembly during multiple intubations. The outer tube shown is a 50 cm tube but it should be clear to others skilled in the art that the present invention is not limited to any particular tube length. The elongated tube 14 may also include circumferentially spaced coils in a portion of the tube. The coils add strength to the tube during insertion.

The first handle 18 has a base 18b, a proximal end 19a and a distal end 19b. The base 18b is constructed of a hard plastic and may be covered with a foam material 20 for helping an operator grip the handle. As seen in FIGS. 1 and 2a, the proximal end of the first handle 18 is a threaded opening 23.

The inner tube 10 includes an elongated tube 24, a tapered cuff 26 disposed on the distal end of the elongated tube 24, and a second handle 28. The elongated tube 24 may be constructed of any suitable polymer, such as for example, extruded polyvinyl chloride. As illustrated, the elongated tube 24 is illustrated without internal coils or springs of any kind. The lack of coils reduces costs and increases the clearance room for the endoscope, although coils could be used in the practice of the present invention to add strength to the inner tube. The inner tube shown is clear, however it may be frosted. Such a treatment reduces the friction between the inner tube and the outer tube, as well as between the inner tube and the endoscope.

Referring now to FIG. 2b, an enlarged cross-sectional view of the assembly of FIG. 2a is shown with an endoscope 30 inserted co-axially through the inner tube 24. The elongated tube 24 has an inner diameter $D_1$ greater than an outer diameter $D_2$ of the illustrated conventional endoscope. As a result, a clearance exists between the inner tube 24 and the endoscope 30 along nearly the entire length of the inner tube. This clearance reduces friction during insertion of the endoscope 30 within the inner tube 24.

The size relationship between the outer tube and the inner tube is also designed to reduce friction. The outer diameter of the inner tube is less than the inner diameter of the outer tube. Consequently, when the inner tube is co-axially inserted within the outer tube as shown in FIG. 2a, a clearance exists between the inner tube and the outer tube along a length of the inner tube. This clearance facilitates the initial insertion by the physician of the inner tube 10 within the outer tube 12.

As mentioned, the inner tube 10 shown in FIG. 1 includes a cuff. The tapered cuff 26 is fixed onto the distal end of the elongated tube 24 by bonding or some other suitable known method. As shown in FIGS. 1 and 2a, the cuff 26 overlaps the elongated tube 24 by a length $L_1$. The cuff 26 has a tapered portion 32 that defines an inner cuff diameter $D_3$. This inner diameter is sized such that the cuff 26 forms a seal around the outer surface of the endoscope 30 inserted therethrough. The tapered cuff 26 may be constructed from various methods, such as for example, from a dip molded process or injection molding. Further, the elongated tube 24 and cuff 26 may be constructed as an integral piece.

Figure 2C:
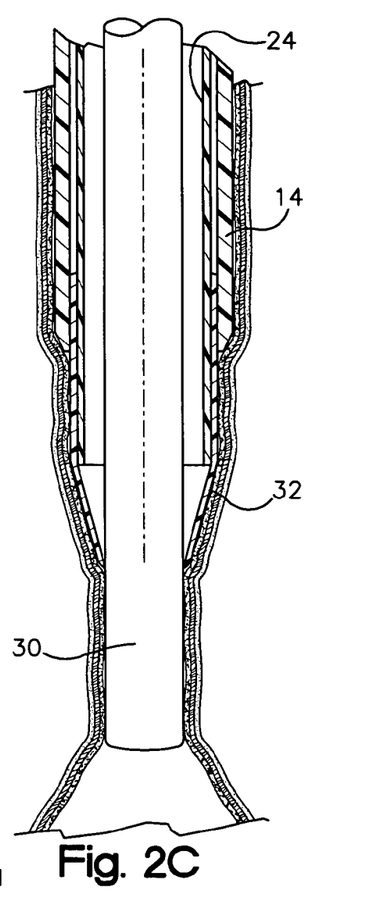
FIG. 2c is an enlarged cross-sectional view of the bottom portion of FIG. 2b, showing the position of the outer tube, inner tube and endoscope in relation to tissue layers of the esophagus.
Figure 3:
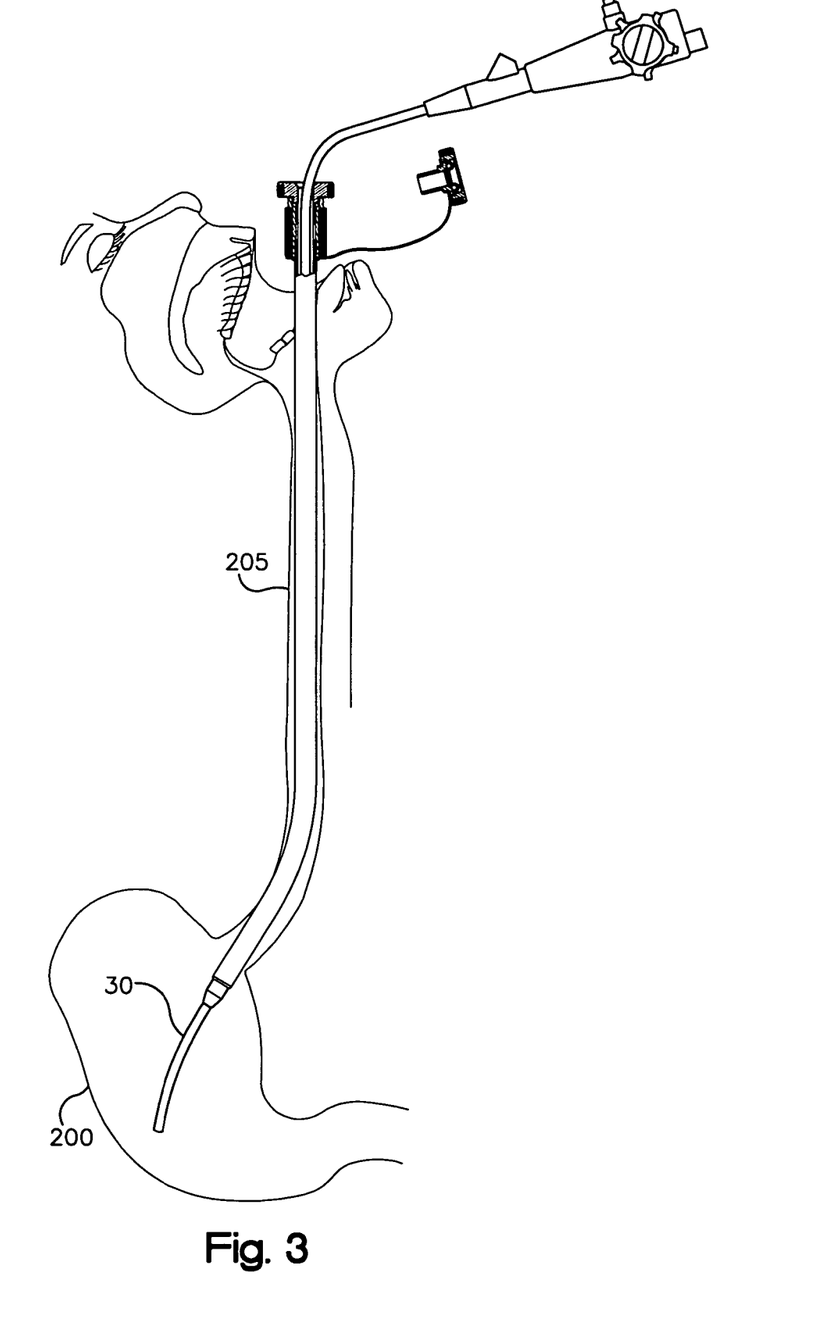
FIG. 3 is a schematic view of the device of FIG. 1, showing a human patient intubated with the assembly shown in FIG. 2b.

FIG. 3 is a schematic view showing a human patient intubated with the assembly shown in FIG. 2b. When the distal end 11 of the inner tube 10 is inserted beyond the distal end 13 of the outer tube 12, the inner tube distal end and the outer tube distal end form a seal. In the assembled position shown in FIG. 2a and 2b, a distal end of the outer tube and a distal end of the inner tube are sealed, preventing any damage or pinching of the esophagus tissue during insertion. FIG. 2c is an enlarged cross-sectional view of the bottom portion of FIG. 2b. The position of the outer tube 14, inner tube 24 and endoscope 30 in relation to tissue layers of the esophagus 205 are shown. The layers, i.e., the mucosa 27a, the submucosa 27b, and the muscularis 27c are illustrated on either side of the device. No pinching or tearing of tissue has occurred.

Figure 2D:
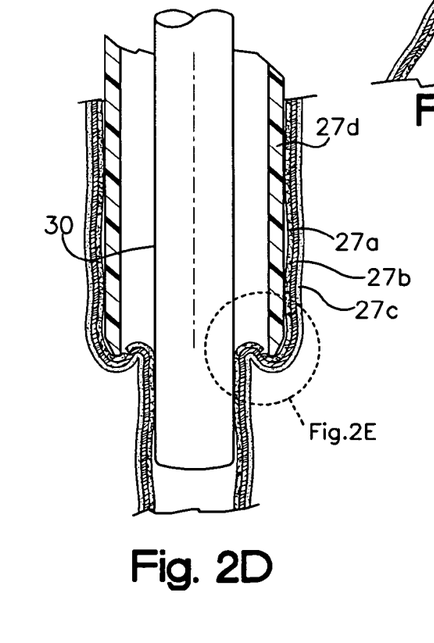
FIG. 2d is a cross-sectional view of a prior art device, showing the position of an over tube and an endoscope in relation to tissue layers of the esophagus.
Figure 2E:
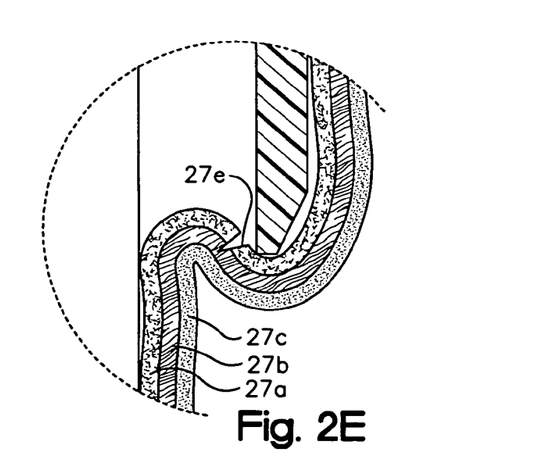
FIG. 2e is a cross-sectional view of the designated circle area of FIG. 2d.

Referring now to FIG. 2d, a cross-sectional view of a prior art device is shown. Specifically, the position of a prior art overtube 27d and an endoscope 30 are illustrated in relation to tissue layers 27a, 27b, 27c of the esophagus. In this design, the layers are allowed to curl back toward the mouth in an area between the endoscope 30 and the overtube 27d. Tissue in this area is prone to pinching. A typical result is illustrated in FIG. 2e, which is a cross-sectional view of the designated circle area of FIG. 2d. A "V-shaped" tear 27e extending through the mucosa 27a and into the submucosa 27b layer is shown. Other shear, tear and pinch patterns are known in the prior art, such as for example, a complete tearing through all three layers.

As mentioned and again referring to FIG. 2a, the inner tube 10 includes a second handle 28 at a distal end of the elongated tube 24. The second handle 28 has a base 28b, a proximal end 29a and a distal end 29b. The base 28b is constructed of a hard plastic and may be covered with a foam grip material 40 for helping an operator grip the handle 28, such as for example, when connecting the second handle 28 to the first handle 18.

As seen in FIG. 1, the distal end of the first handle 18 includes an externally threaded portion 42. When the distal end 11 of the inner tube 10 is inserted beyond the distal end 13 of the outer tube 12, the threaded portion 23 in the first handle 18 proximal end 19a can be easily connected to the threaded portion 42 in the second handle 28 distal end 29b. As such, the first handle 18 is distal to the second handle 28.

Still referring to FIG. 2a, a seal cap 50 is shown connected to the outer tube 12 by a tether 52. The cap 50 is connected at a location adjacent the first handle 18 distal end 19b. A plastic ring 54 is disposed at either end of the tether 52. The tether 52 retains the cap 50 within proximity of the handle 18 when not in a sealed position.

Figure 4A:
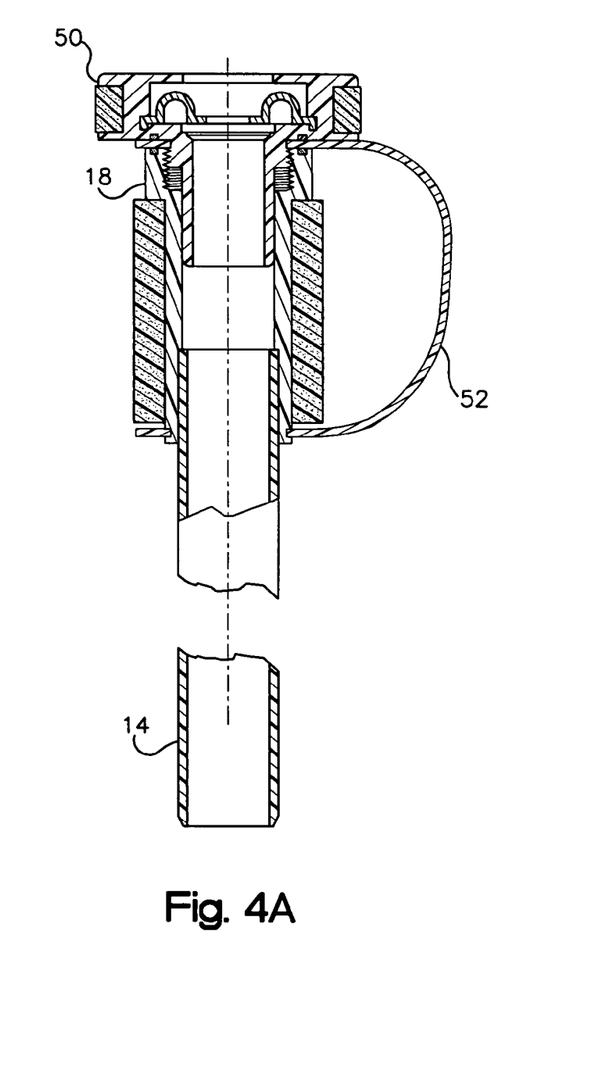
FIG. 4a is an enlarged cross-sectional view of the assembly of FIG. 2b, showing the inner tube and endoscope removed and a tethered cap installed on the proximal end of the outer tube.

The cap 50 has a base 50b, a proximal end 55a and a distal end 55b. The base 50b is constructed of a hard plastic and may be covered with a foam material 56 for ease of use. As seen in FIG. 2a, the base 50b includes a protruding portion 58 that can be inserted directly into the outer tube 12 proximal end 19a of the first handle 18. The proximal end of the protrusion 58 includes an externally threaded portion 60 for connection to the threaded portion 23 in the first handle 18 proximal end 19a, as shown in FIG. 4a.

Figures 5A, 5B:
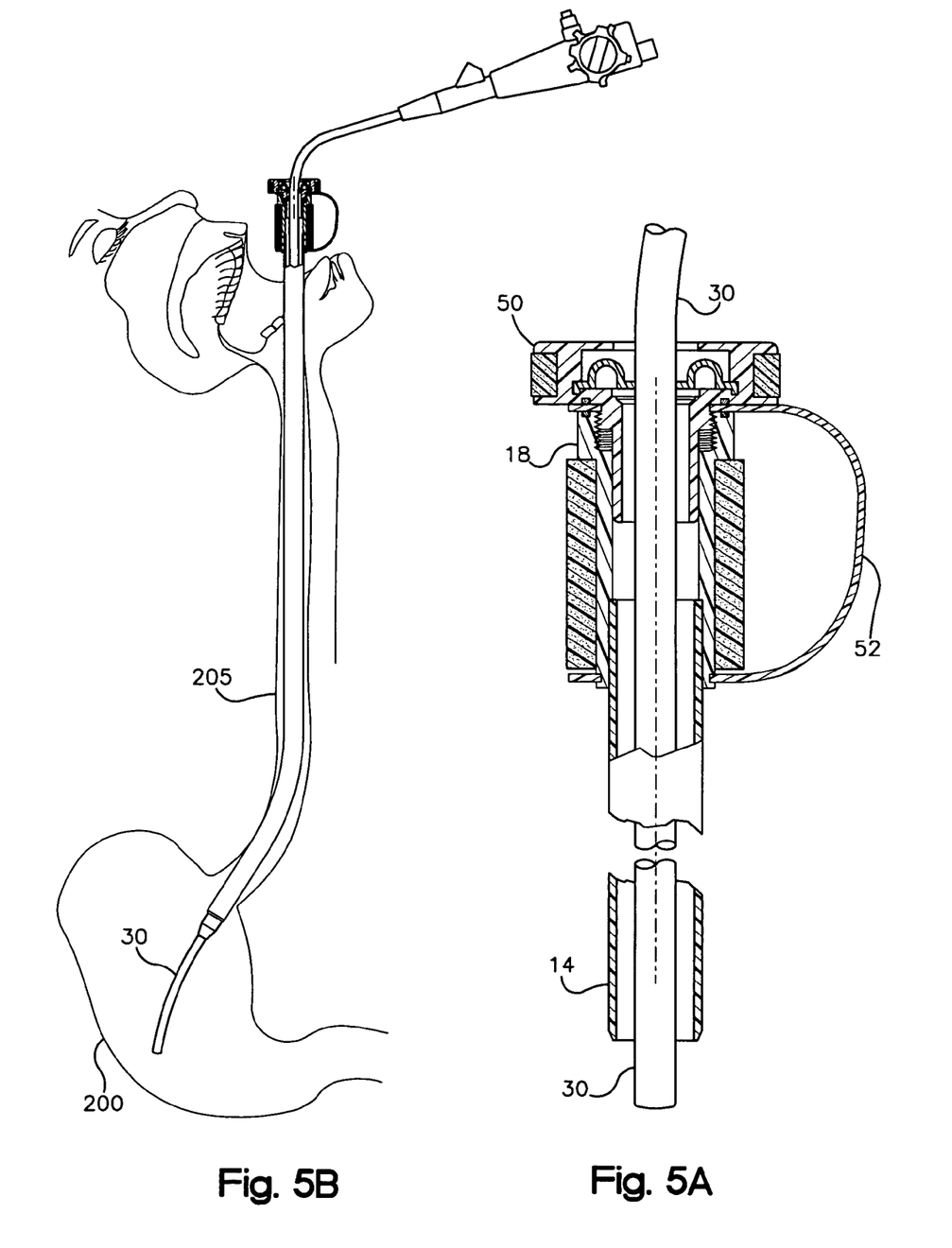

The seal cap as shown includes a flexible seal 62 having a center aperture 64. The seal 62 aperture 64 is sized to form a seal around the outer surface of an endoscope inserted therethrough. A seal cap 50 installed onto an outer tube 12 is shown in FIG. 5a with the inner tube 10 removed. As shown, a seal is formed between the seal 60 and the endoscope 30. In this position, the endoscope 30 is free to laterally move within a length of the outer tube. A seal is maintained around the endoscope outer surface during lateral movement of the endoscope in either direction. Consequently, no venting occurs between the endoscope and the seal. FIG. 5b shows schematic view of a human patient intubated with the assembly shown in FIG. 5a.

Figure 12:
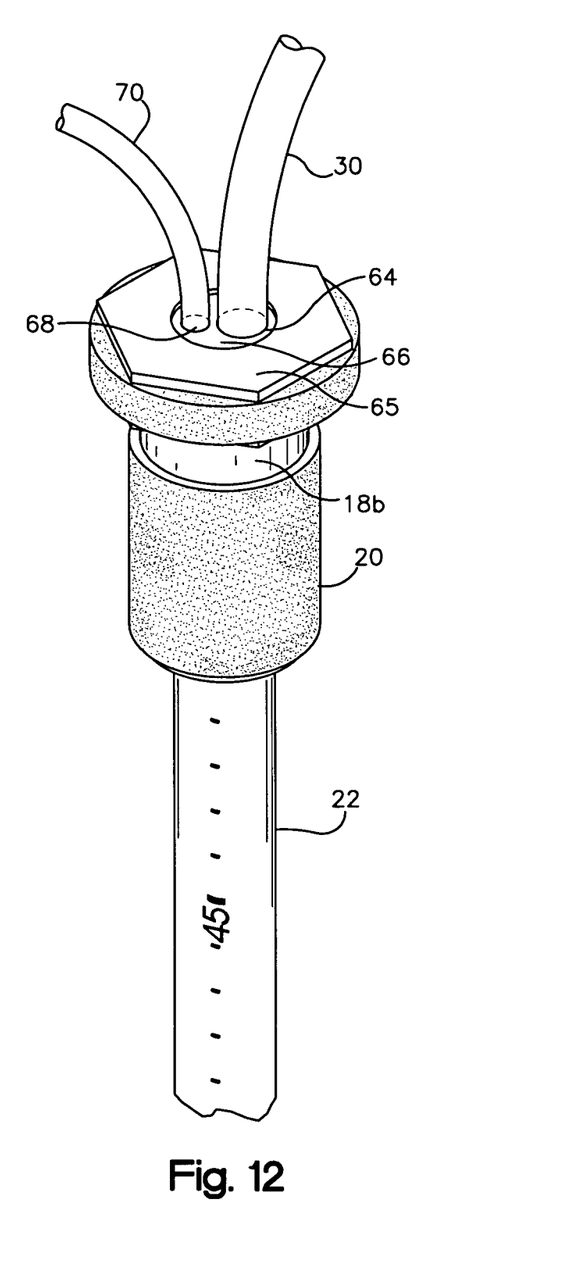
FIG. 12 is a perspective assembly view of a portion of an overtube device constructed in accordance with yet another embodiment of the present invention, showing an alternative proximal cap installed on the proximal end of the outer tube.

The cap 50 may include more than one seal or include a seal having more than one aperture. FIG. 12 is a perspective assembly view of alternative cap 65 of the present invention. The cap 65 includes a seal 66 having two apertures, a first aperture 64 for insertion of an endoscope 30 and a second aperture 68 for insertion of a second endoscopic instrument 70, such as for example, a snare, a net, or a suction device. As shown, a seal is formed between the seal 66 and the endoscope 30 and between the seal 66 and the instrument 70.

Figure 6:
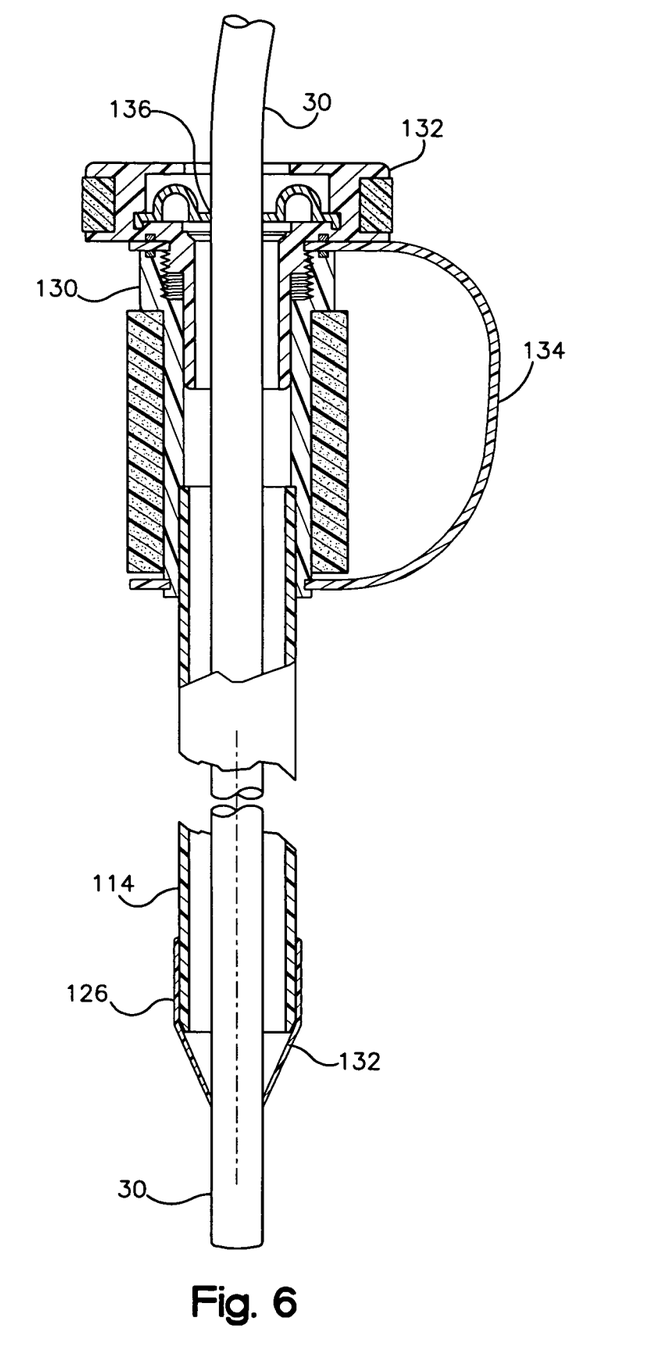
FIG. 6 is a cross-sectional view of another embodiment of the present invention, showing an endoscope inserted through a tapered distal portion of an outer tube.

FIG. 6 is a cross-sectional view of another embodiment of the present invention. As shown, an endoscope 30 is inserted through an outer tube 114. A cuff 126 having a tapered portion 132 is glued onto the distal end of the outer tube 114. The tapered cuff 126 forms a seal around the outer surface of an endoscope 30 inserted therethrough as shown. A handle 130 is fixed to the proximal end of the outer tube 114. The device includes a cap 132 connected to the outer tube 114 by a tether 134. The cap 132 is removably connectable to the proximal end of the handle 130. The cap has an aperture 136 adapted to form a seal around the outer surface of the endoscope 30 inserted therethrough as shown.

Figure 7A:
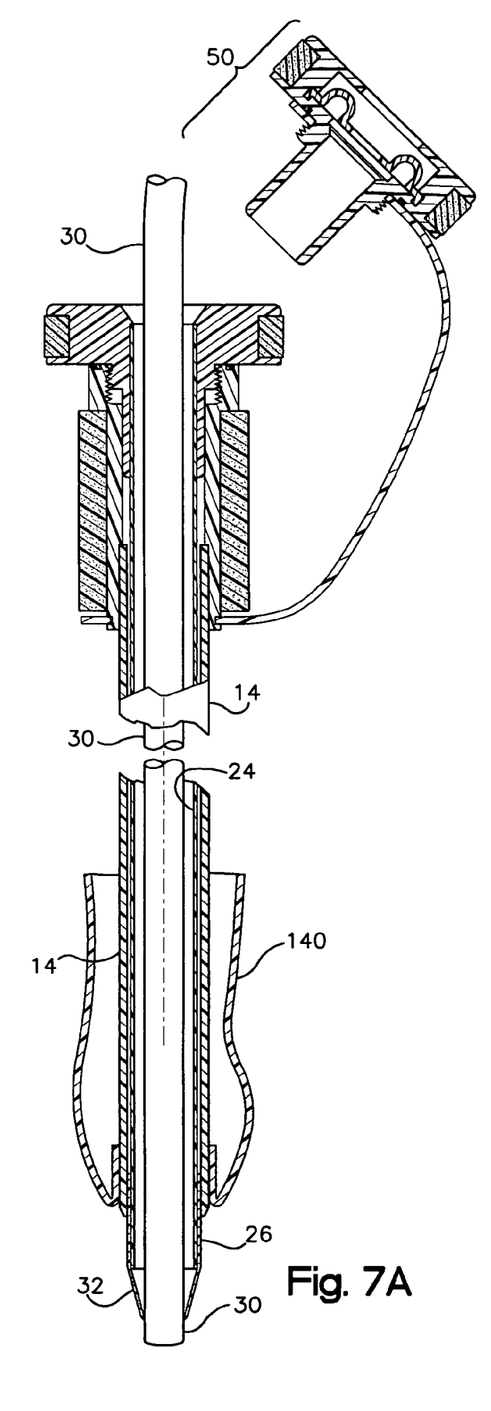
FIG. 7a is a cross-sectional view of yet another embodiment of the present invention, showing the inner tube and outer tube in an assembled position with an endoscope inserted through the inner tube and a protective hood in an inverted position and connected to the distal end of the outer tube.

FIG. 7a is a cross-sectional view of yet another embodiment of the present invention. An elongated inner tube 24 is shown inserted into an elongated outer tube 14 with an endoscope 30 inserted through the inner tube. At the distal end of the outer tube 14, a protective hood 140 is shown in an inverted position fixed to the outer tube. In the practice of the present invention, the hood is used in the capture of foreign objects in the gastro-intestinal tract. Specifically, the hood protects the esophagus, trachea and throat when the object is being remove. Therefore, the hood 140 may be constructed of any suitable tear resistant polymer of sufficient strength. A non-latex material is preferred to prevent irritation or reaction caused by allergies.

Figure 7B:
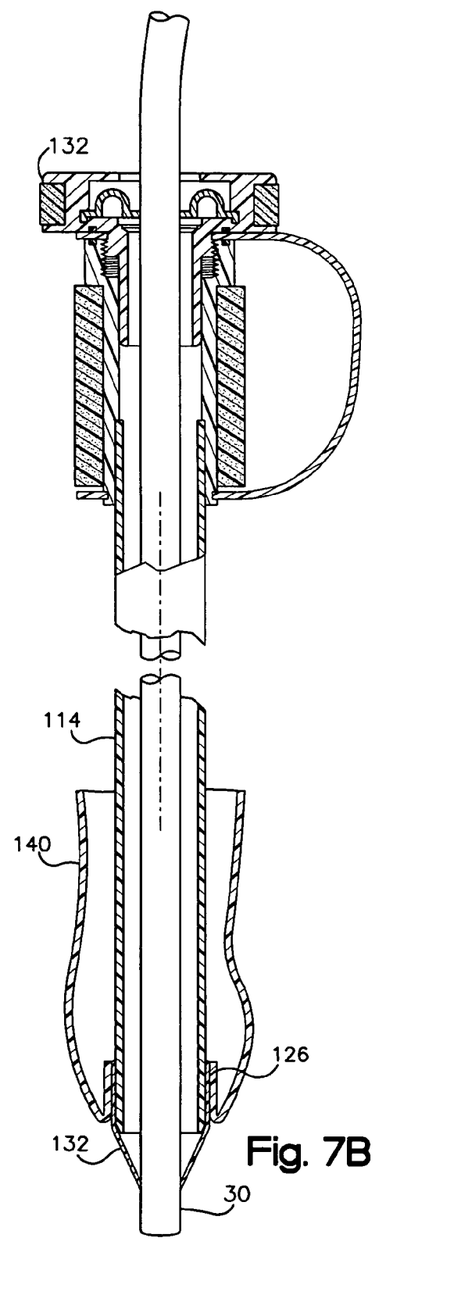
FIG. 7b is a cross-sectional view of yet another embodiment of the present invention, showing an endoscope inserted through the outer tube and a protective hood in an inverted position and connected to the distal end of the outer tube.

Another embodiment of the present invention that includes a hood is shown in FIG. 7b. An endoscope 30 is shown inserted through an outer tube 114. A protective hood 140 is fixed to the distal end of the outer tube 114. The hood 140 is illustrated in an inverted position. For exemplary purposes, the removal of a razor blade using the device of FIG. 7b will be discussed.

Figure 8:
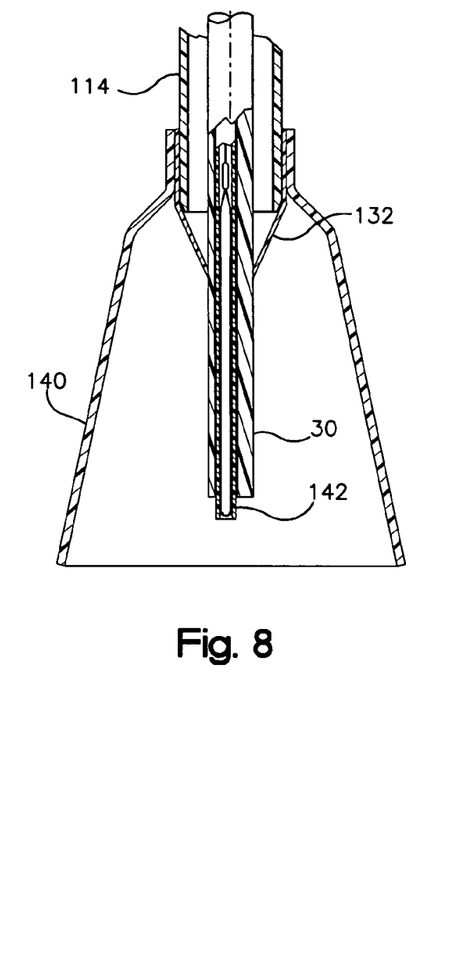
FIG. 8 is a cross-sectional view of device of FIG. 7b, showing the protective hood in a forward position.

FIG. 8 is a cross-sectional view of device of FIG. 7b, showing the protective hood 140 in a forward position. At the beginning of the removal process, a physician will insert the distal end of the device into the stomach. A seal is formed between the endoscope 30 and the tapered cuff 132. As a result, no pinching or tearing of the esophagus tissue occurs during initial insertion.

Within the stomach, it is possible to manipulate the hood to the forward position shown in FIG. 8 by pulling back on the device. Once the hood is in this forward position, an endoscope 30 may be extended into the hood. A snare instrument 142 is shown within an instrument channel of the endoscope 30.

Figure 9:
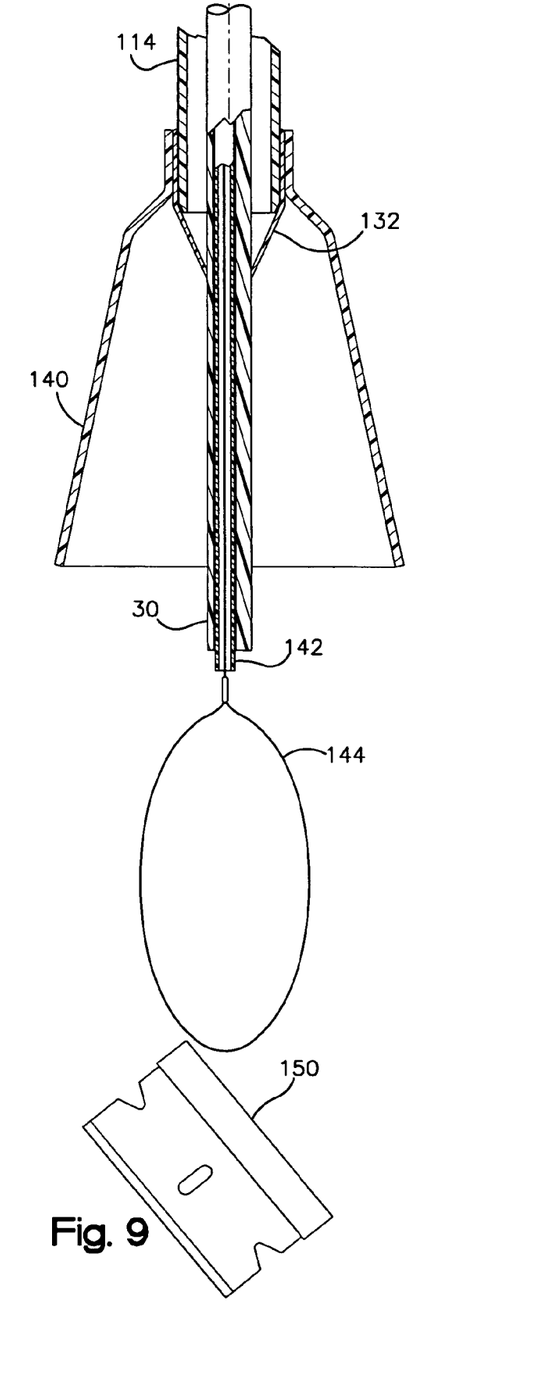
FIG. 9 is a cross-sectional view of device of FIG. 7b, showing a snare instrument being used to capture a foreign object.
Figure 10:
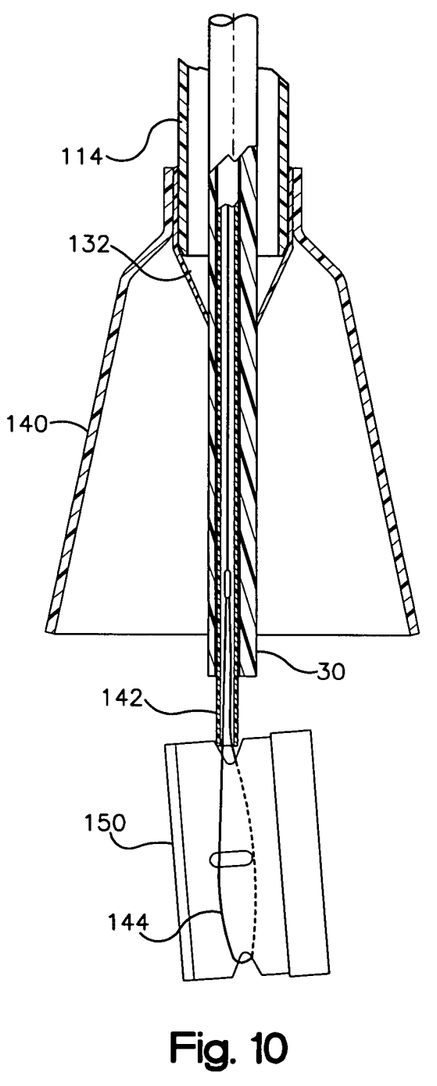
FIG. 10 is a cross-sectional view of device of FIG. 7b, showing the foreign objected within the snare.
Figure 11:
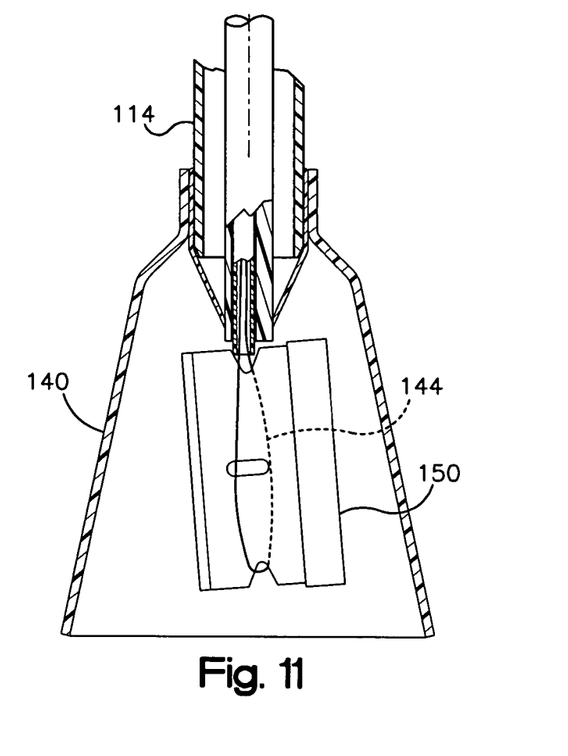
FIG. 11 is a cross-sectional view of device of FIG. 7b, showing the snare collapsed within the protective hood.

The physical capture of the razor blade 150 is illustrated in FIGS. 9-11. In FIG. 9, the loop 144 of the snare instrument 142 is expanded toward the razor blade. FIG. 10 shows the razor blade 150 within the snare loop 144. In FIG. 11, the snare loop is shown retracted and collapsed back within the protective hood 144. Throughout the entire capture process, a seal is maintained between the endoscope 30 and the distal end of the outer tube 114.

A method of use of an embodiment of the present invention will be discussed. The method is for intubating a human patient as part of an endoscopic procedure. An inner tube 10 and an outer tube 12, as illustrated in FIG. 1, are selected. The inner tube 10 is inserted through an entire length of the outer tube 12 such that the inner tube 10 distal end extends beyond the outer tube 12 distal end, as shown in FIG. 2a. This insertion step forms a seal between the tubes 10, 12 at the distal end of the assembly.

The next method step is inserting an endoscope 30 within the inner tube 10, as shown in FIG. 2b. After an endoscope is inserted within the inner tube 10, a seal is then created at the proximal ends by a connection, e.g., a threaded cap, a snap fit connection, or a bayonet-style connection. Next, the device is delivered to the desired internal location as shown in FIG. 3. In this example, the device is shown inserted through the esophagus 205 to the stomach 200. The method includes preventing any esophagus tissue layers from being pinched between the inner tube and the outer tube distal end during intubation, or between the inner tube tapered distal end and the endoscope. An illustration of desired insertion effect is shown in FIG. 2c.

Next, the proximal connection is released and the inner tube 10 and endoscope 30 are removed. The outer tube 12 stays in place. Any connection structure that allows for the inner tube 10 to be disengaged from the outer tube 12 in an efficient, quick and coordinated manner is suitable. Exemplary structure include a snap fit connection and a quarter turn threaded connection.

Figure 4B:
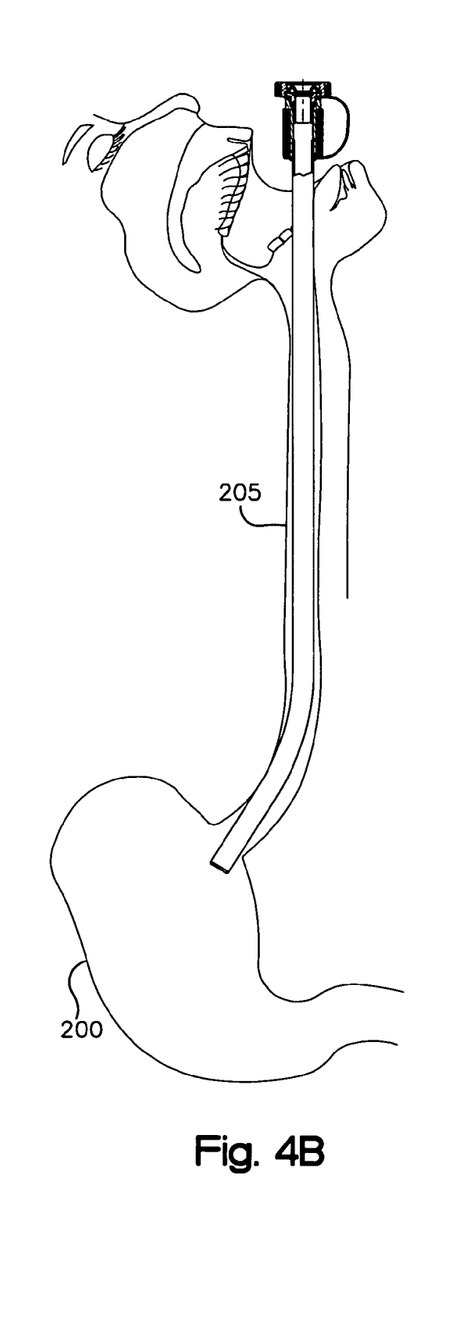

A cap is subsequently connected to the proximal end of the outer tube 12. An exemplary threaded connection between the cap and outer tube 12 is shown in FIG. 4a. After this connection is made, the device remains in place as shown in FIG. 4b.

The method includes the step of inserting the endoscope 30 through an aperture in the cap 50 to form a seal, as shown in FIG. 5a. In FIG. 5b, an endoscope 30 is shown inserted through an entire length of the outer tube 12 to beyond the outer tube distal end. In this position, the physician can perform the substantive portion of the endoscopic procedure.

The method may include multiple intubations, i.e., repetitive removal and insertion of the endoscope during the substantive procedure. Repetitive insertions may be required for certain endoscopic procedures. The outer tube 12 remains in place during the entire procedure to protect the tissue of the esophagus.

While several embodiments of the invention have been illustrated and described, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the annexed claims.

What is claimed:

1. An overtube device for use in intubating a human subject with an endoscope, the device comprising:
   an outer tube comprising a first elongated tube having a distal end, a proximal end, and a first handle disposed on the proximal end; and
   an inner tube comprising a second elongated tube having a distal end, a proximal end, a second handle disposed on the proximal end, and a cuff fixed to the distal end, the cuff comprising a proximal cylindrical portion and a distal conical portion, the conical portion reducing in diameter in a distal direction and adapted to seal around the endoscope inserted in the distal direction therethrough, wherein the overtube device and the endoscope form an intubatable assembly;
   wherein an outer diameter of the second handle is greater than an inner diameter of the outer tube to prohibit passage of the second handle into the first elongated tube of the outer tube;
   further wherein the inner tube in an assembled position is inserted through the outer tube such that the second elongated tube extends along a length of the device in the distal direction beyond the distal end of the first elongated tube and beyond a proximal end of the cylindrical portion, the cylindrical portion extends along a length of the device in the proximal direction beyond the distal end of the first elongated tube and in the distal direction beyond the distal end of the first elongated tube, and the conical portion extends along a length of the device in the distal direction beyond the distal end of the second elongated tube;
   further wherein the inner tube in an assembled position defines an elongated chamber concentric with the inner tube and the outer tube, wherein the chamber extends the entire length of the inner tube for removable insertion of an endoscope therein,
   further wherein the first handle has a proximal end and a distal end, the first handle comprises a connection portion disposed on the proximal end and a cylindrical base tube, the first elongated tube substantially extends into and firmly connects with the cylindrical base tube from the distal end,
   further wherein the first elongated tube does not contact the second handle when the inner tube is in an assembled position.

2. The device of claim 1, wherein the first handle forms a threaded connection with the second handle.

3. The device of claim 1, wherein the outer tube comprises length identifying indicia.

4. The device of claim 1, wherein the outer tube comprises circumferentially spaced coils in a portion between the proximal end and the distal end.

5. The device of claim 1, further comprising a cap adapted to connect with a proximal end of the first handle, the cap having an aperture adapted to form a seal around an outer surface of an endoscope inserted therethrough.

6. The device of claim 1, wherein the conical portion of the cuff is adapted to distally seal with the endoscope when the inner tube, the outer tube and the endoscope are in an assembled position.

7. The device of claim 1, wherein the inner tube, the outer tube and the endoscope in an assembled position include sections of decreasing outer diameter in a distal direction, the sections defined by a diameter of the outer tube, a diameter of a cylindrical portion of the cuff, a diameter of a conical portion of the cuff, and a diameter of the endoscope.

8. The device of claim 1, wherein a gap is defined in the assembled position by an outer surface of the second elongated tube and an inner surface of the first elongated tube, the gap extending a length of the device from the second handle to the cuff, and a radial width of the gap is essentially the same as a wall thickness of the cylindrical portion of the cuff.

9. An overtube device for use in intubating a human subject with an endoscope, the device comprising:
   an outer tube comprising a first elongated tube having a distal end, a proximal end, and a first handle disposed on the proximal end; and
   an inner tube comprising a second elongated tube having a distal end, a proximal end, a second handle disposed on the proximal end, and a cuff fixed to the distal end, the cuff comprising a proximal cylindrical portion and a distal conical portion, the conical portion reducing in diameter in a distal direction and adapted to seal around the endoscope inserted in the distal direction therethrough, wherein the overtube device and the endoscope form an intubatable assembly;
   wherein an outer diameter of the second handle is greater than an inner diameter of the outer tube to prohibit passage of the second handle into the first elongated tube of the outer tube;
   further wherein the inner tube in an assembled position is inserted through the outer tube such that each of the first elongated tube, the second elongated tube, and the cylindrical portion radially overlap along a length of the device;
   further wherein the inner tube in an assembled position defines an elongated chamber concentric with the inner tube and the outer tube, wherein the chamber extends the entire length of the inner tube for removable insertion of an endoscope therein, further wherein the first handle has a proximal end and a distal end, the first handle comprises a connection portion disposed on the proximal end and a cylindrical base tube, the first elongated tube substantially extends into and firmly connects with the cylindrical base tube from the distal end, further wherein the first elongated tube does not contact the second handle when the inner tube is in an assembled position.

10. The device of claim 9, wherein a gap is defined in the assembled position by an outer surface of the second elongated tube and an inner surface of the first elongated tube, the gap extending a length of the device from the second handle to the cuff, and a radial width of the gap is essentially the same as a wall thickness of the cylindrical portion of the cuff.

* * * * *